United States Patent
Mondadori et al.

(10) Patent No.: US 6,939,879 B2
(45) Date of Patent: *Sep. 6, 2005

(54) USE OF R (+)-α-(2,3-DIMETHOXYPHENYL)-1-[2-(4-FLUOROPHENYL)ETHYL]-4-PIPERIDINEMETHANOL FOR THE TREATMENT OF SUBSTANCE INDUCED INSOMNIA

(75) Inventors: Cesare Mondadori, Reinach (CH); Stephen M. Sorensen, Chester, NJ (US); Janice M. Hitchcock, Fishers, IN (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 28 days.

This patent is subject to a terminal disclaimer.

(21) Appl. No.: 10/609,751

(22) Filed: Jun. 30, 2003

(65) Prior Publication Data

US 2004/0002516 A1 Jan. 1, 2004

Related U.S. Application Data

(63) Continuation of application No. 09/886,424, filed on Jun. 21, 2001, now Pat. No. 6,613,779, which is a continuation of application No. 09/382,932, filed on Aug. 23, 1999, now Pat. No. 6,277,864.
(60) Provisional application No. 60/155,214, filed on Aug. 28, 1998.

(51) Int. Cl.$^7$ ............................................. A61K 31/445
(52) U.S. Cl. ..................................... 514/317; 514/317
(58) Field of Search ......................................... 514/317

(56) References Cited

U.S. PATENT DOCUMENTS

| | | |
|---|---|---|
| 4,783,471 A | 11/1988 | Carr et al. |
| 4,877,798 A | 10/1989 | Sorensen |
| 4,908,369 A | 3/1990 | Schechter et al. |
| 4,912,117 A | 3/1990 | Carr et al. |
| 5,021,428 A | 6/1991 | Carr et al. |
| 5,064,838 A | 11/1991 | Carr et al. |
| 5,106,855 A | 4/1992 | McLees |
| 5,134,149 A | 7/1992 | Carr et al. |
| 5,169,096 A | 12/1992 | Carr et al. |
| 5,561,144 A | 10/1996 | Carr et al. |
| 5,618,824 A | 4/1997 | Schmidt et al. |
| 5,700,812 A | 12/1997 | Carr et al. |
| 5,700,813 A | 12/1997 | Carr et al. |
| 5,721,249 A | 2/1998 | Carr et al. |

FOREIGN PATENT DOCUMENTS

| | | |
|---|---|---|
| EP | 0317933 | 5/1989 |
| EP | 0319962 | 6/1989 |
| EP | 0337136 | 10/1989 |
| WO | WO 97/34603 | 9/1997 |

OTHER PUBLICATIONS

Dorland's Illustrated Medical Dictionary, 1965, p 1606.*

A. John Rush et al., Comparative Effects of Nefazodone and Fluoxetine on Sleep in Outpatients with Major Depressive Disorder, Society of Biological Psychiatry (1998, pp. 3–14, vol. 44).

A. L. Sharpley et al., Slow Wave Sleep in Humans: Role of 5–HT2A and 5–HT2A Receptors, Neuropharmacology (1994, pp. 467–471, vol. 33, No. 3/4).

A. L. Sharpley et al., Dose–related effects of selective 5–HT2 Receptor Antagonists on Slow Wave Sleep in Humans, Psychopharmacology (1990, pp. 568–569, vol. 101).

Alexander A. Borbely et al., Effect of Ritanserin on Sleep Stages and Sleep EEG in the Rat, European Journal of Pharmacology (1988, pp. 275–278, vol. 156).

Andre Reyntjens et al., Thymosthenic Effects of Ritanserin (R 55667), a Centrally Acting Serotonin–S2 Receptor Blocker, Drug Development Research (1986, pp. 205–211, vol. 8).

C. Idzikowski, F.J. et al., 5–Hydroxytryptamine–2 antagonist increases human slow wave sleep, Brain Research (1986, pp. 164–168, vol. 378).

D. Morin et al., Depressant effect of raphe stimulation on inspiratory activity of the hypoglossal nerve; in vitro study in the newborn rat, Neuroscience Letters (1990, pp. 299–303, vol. 116).

D. Morin et al., Serotonergic influences on central respiratory activity: an in vitro study the newborn rat, Brain Research (1990, pp. 281–287, vol. 535).

David W. Hudgel, Treatment of Obstructive Sleep Apnea, Reviews (1996, pp. 1346–1358, vol. 109, No. 5).

Didier Morin et al., 5–Hydroxytryptamine modulates central respiratory activity in the newborn rat: an in vitro study, European Journal of Pharmacology, (1991, pp. 89–95, vol. 192).

Didier Morin et al., Compared effects of serotonin on cervical and hypoglossal inspiratory activities: an in vitro study in the newborn rat, Journal of Physiology (1992, pp. 605–629, vol. 451).

(Continued)

Primary Examiner—Rebecca Cook
(74) Attorney, Agent, or Firm—Balaram Gupta

(57) ABSTRACT

A method of providing symptomatic relief from sleep induced insomnia in a patient comprising administering an effective amount of R-(+)-α-(2,3-Dimethoxyphenyl)-1-[2-(4-fluorophenyl)ethyl]-4-piperidinemethanol or a pharmaceutically acceptable salt thereof to a patient in need of such treatment.

14 Claims, No Drawings

OTHER PUBLICATIONS

Didier Morin, Compared effects of serotonin on the inspiratory activity of glossopharyngeal, vagal, hypoglossal and cervical motoneurons in neonatal rat brain stem–spinal cord preparations, Neuroscience Letters, (1993, pp. 61–64, vol. 160).

Douglas A. Hanzel et al., Response of Obstructive Sleep Apnea to Fluoxetine and Protriptyline, Chest (Aug. 1991, pp. 416–421, vol. 100, No. 2).

E. Di Pasquale et al., Serotonergic modulation of the respiratory rhythm generator at birth: an in vitro study in the rat, Neuroscience Letters (1992, pp. 91–95 vol. 143).

Eric Di Pasquale et al., Endogenous Serotonin modulates the fetal respiratory rhythm: an in vitro study in the rat, Developmental Brain Research ( 1994, pp. 222–232, vol. 80).

Eric Di Pasquale et al., In vitro study of central respiratory–like activity of the fetal rat, Experimental Brain Research (1992, pp. 459–464, vol. 89).

Eric Di Pasquale et al., Involvement of the rostral ventro-–lateral medulla in respiratory rhythm genesis during the peri–natal period; an in vitro study in newborn and fetal rats, Developmental Brain Research (1994, pp. 243–252, vol. 78).

Frank C. Tortella et al., Suppressant Effects of Selective 5–HT2 Antagonists on Rapid Eye Movement Sleep in Rats, Brain Research (1989, pp. 294–300, vol. 485).

G. Hilaire et al., A Cross–Correlation Study of Interactions Among Respiratory Neurons of Dorsal, Ventral and Retrofacial Groups In Cat Medulla, Brain Research, (1984, pp. 19–31, vol. 302).

G. Hilaire et al., Central Respiratory Drive and Recruitment Order of Phrenic and Inspitatory Laryngeal Motoneurones, Respiratory Physiology (1983, pp. 341–359, vol. 51).

G. Hilaire et al., Functional Significance of the dorsal respiratory group in adult and newborn rats; in vivo and in vitro studies, Neuroscience Letters (1990, pp. 133–138, vol. 111).

G. Hilaire et al., Possible modulation of the medullary respiratory rhythm generator by the noradrenergic A5, area; an in vitro study in the newborn rat, Brain Research (1989, pp. 325–332, vol. 485).

G. Hilaire et al., Spontaneous Respiratory Activity of Phrenic And Intercostal Renshaw Cells, Neuroscience (1983, pp. 97–101, vol. 43).

Gerard Hilaire et al., Changes in Serotonin Metabolism May Elicit Obstructive Apnoea in the Newborn Rat, Journal of Physiology (1993, pp. 367–382, vol. 466).

H.S. Schmidt, L–Tryptophan in the Treatment of Impaired Respiration in Sleep, Bulletin, European Physiopath (1983, pp. 625–629, vol. 19).

J. C. Hendricks et al., The English Bulldog: a natural model of sleep–disordered breathing, The American Physiological Society (1987, pp. 1344–1350, vol. 161, No. 7567).

J.M. Da Roza Davis et al., Slow wave sleep and 5–HT2 Receptor Sensitivity in Generalised Anxiety disorder: a pilot study with ritanserin, Psychopharmacology, (1992, pp. 387–389, vol. 108).

Jean–Louis Brassard et al., A Selective 5–HT1 Agonist, RU 24969, Increases Locus Coeruleus Catechol Metabolic and Neuronal Activity, Neurochem. Int. (1987, pp. 89–94, vol. 10, No. 1).

Joan C. Hendricks et al., Phasic Respiratory Muscle Patterns and Sleep–Disordered Breathing during Rapid Eye Movement Sleep in the English Bulldog, American Review of Respiratory (1991, pp. 1112–1120, vol. 144).

Joan C. Hendricks et al., Upper Airway Dilating Muscle Hyperactivity during Non–Rapid Eye Movement Sleep in English Bulldogs, American Review of Respiratory (1993, pp. 185–194, vol. 148).

L. Quintin et al., Variations in 3,4–Dihydroxyphenylacetic Acid Concentration are Correlated to Single Cell Firing Changes in the Rat Locus Coerules, Neuroscience (1986, pp. 889–899, vol. 18, No. 4).

Liv Sommerfelt et al., The 5–HT2 Antagonist Ritanserin Decreases Sleep in Cats, Sleep (1993, pp. 15–22, vol. 16, No. 1).

Luc Quintin et al., Catecholamine Metabolism in the Rat Locus Coeruleus as Studied by in Vivo Differential Pulse Voltammetry, III. Evidence for the Existence of an alpha 2–Adrenergic Tonic Inhibition in Behaving Rats, Brain Research (1986, pp. 235–245, vol. 375).

Luc Quintini et al., Clonidine Modulates Locus Coeruleus Metabolic Hyperactivity Induced by Stress in Behaving rats, Brain Research (1986, pp. 366–369, vol. 362).

M. Dahlitz et al., Treatment of Insomnia with Ritanserin, Laucet (1990, pp. 379, vol. 336).

M. Khatib et al., Excitatory Interactions Between Phrenic Motoneurons in the Cat Exp. Brain Res (1986, pp. 273–280, vol. 62).

Matcheri S. Keshavan et al., Delta Sleep Deficits in Schizophrenia, Arch Gen Psychiatry (1998, pp. 443–448, vol. 55).

P. Gauthier et al., Onset and Control of Expiratory Laryngeal Discharge: Cross–Correlation Analysis, Respiration Physiology (1983, pp. 67–77, vol. 54).

Peter D. Nowell et al., Benzodiazepines and Zolpidem for Chronic Insomnia, Jama (1997, pp. 2170–2177, vol. 278, No. 24).

R. Kirov et al., Ritanserin–Induced Changes in Sleep–Waking Phases in Rats, Acta Physiologica and Pharmacologica Bulgarica (1995, pp. 87–92, vol. 21, No. 4).

R. Monteau et al., Differential effects of serotonin on respiratory activity of hypoglossal and cervical motoneurons; and in vitro study on the newborn rat, Neuoscience Letters, (1990, pp. 127–132, vol. 111).

R. Monteau et al., Effects of N–Methyl–D–Aspartate (NMDA) antagonist MK–801 on Breathing pattern in rats, Neuroscience Letters, (1990, pp. 134–139, vol. 109).

R. Moneau et al., Pneumotaxic centre and apneustic breathing: interspecies differences between rat and cat, Neuroscience Letters, (1989, pp. 311–316, vol. 99).

Roger Monteau et al., Further evidence that various 5–HT receptor subtypes modulate central respiratory activity: in vitro studies with SR 46349B, European Journal of Pharmacology (1994, pp. 71–74, vol. 259).

S. Errchidi et al., Permanent Release of Noradrenaline Modulates Respiratory Frequency in the Newborn Rat: an in vitro study, Journal of Physiology (1990, pp. 497–510, vol. 429).

Sigrid C. Veasey et al., The effects of serotonin Antagonists in an Animal Model of Sleep–Disordered Breathing, American Journal of Respiratory and Critical Care Medicine (1996, pp. 776–786, vol. 153).

Susan M. Harding,, Sleep in Fibromyalgia Patients: Subjective and Objective Findings, The American Journal of the Medical Sciences (pp. 367–376, vol. 315, No. 6).

Y.D. Lapierre et al., Dysthymia and Serotonin, International Clinical Psychopharmacology (1993, pp. 87–90, vol. 8 Supplement 2).

What do Amidepressant Effects on Sleep Tell Us about Pathways to Treatment Response?, Society of Biological Pyschiatry (1998, pp. 1–2, vol. 44).

Sramck, et al., A Bridging Study of MDL100,907 in Schizophrenic Patients, Abstract, 1996, ACNP Annual Meeting Presentation.

David W. Hudgel, Treatment Of Obstructive Sleep Apnea, Chest (1996, pp. 1346–1358, vol. 105, No. 5).

A. C. Declerck, et al., Increase In Slow–Wave Sleep In Humans With The Serotonin–S2 Antagonist Ritanserin, Current Therapeutic Research, (1987, pp. 427–431, vol. 41, No. 4).

Bristol–Myers Squibb, In Depressed Patients Is Improved With Dutonin, Sleep.

Francis P. Miller et al., Piperidinylmethanol derivatives for the treatment anxiety, American Chemical Society (1989)—Abstract only, CA H2H–72341.

John H. Kehne et al., Predinioal Characterization of the Potential of the Puriative Atypical Antisychotic MDL 100, 907 as a Potent 5–HT2A Antagonist with a Favorable CNS Safety Profile, The Journal of Pharmacology and Experimental Therapeutics (1996, pp. 968–981, vol. 277, No. 2) Abstract Only.

Kirstine Adam et al., Effects of Repeated Ritanserin on Middle–Aged Poor Sleepers, Psychopharmacology (1989, pp. 219–221, vol. 99).

M. Dahlitz et al., Treatment of Insomina with fütanserin, Laucet (1990, pp. 379, vol. 336).

M. Khatib et al., Excilatory Interactions between Phrenic Motoneurons: Intracellular Study in the Cat, Exp. Brain Res (1989, pp. 131–138, vol. 74).

Peter D. Nowell et al., Benzodiazepines and Zolpidem for Chronic Insomnia, Journal of American Medical Assn. (1997, pp. 2170–2177, vol. 278, No. 24).

* cited by examiner

USE OF R (+)-α-(2,3-DIMETHOXYPHENYL)-1-[2-(4-FLUOROPHENYL)ETHYL]-4-PIPERIDINEMETHANOL FOR THE TREATMENT OF SUBSTANCE INDUCED INSOMNIA

CROSS REFERENCE TO RELATED CASES

This application is a continuation of U.S. application Ser. No. 09/886,424, filed, Jun. 21, 2001 now U.S. Pat. No. 6,613,779, now allowed, which is a continuation of U.S. application Ser. No. 09/382,932, filed, Aug. 25, 1999, now U.S. Pat. No. 6,277,864 B1, issued Aug. 21, 2001, which claims the benefit of U.S. Provisional Application No. 60/155,214, filed, Aug. 28, 1998 now abandoned.

FIELD OF THE INVENTION

The present invention relates to the therapeutic use of a compound for the treatment of Sleep Disorders (insomnia and obstructive sleep apnea).

BACKGROUND OF THE INVENTION

The compound R-(+)-α-(2,3-Dimethoxyphenyl)-1-[2-(4-fluorophenyl)ethyl]-4-piperidinemethanol (hereafter referred to as the "COMPOUND") is a 5HT2a antagonist useful in the treatment of a variety of disorders. U.S. Pat. No. 5,169,096 claimed compounds having a generic scope which encompassed the COMPOUND and disclosed uses of the treatment of anorexia nervosa, variant angina, Raynaud's phenomenon, coronary vasospasms, prophylactic treatment of migraine, cardiovascular diseases such as hypertension, peripheral vascular disease, thrombotic episodes, cardiopulmonary emergencies and arrythmias, and has anesthetic properties. See also U.S. Pat. Nos. 4,783,471; 4,912,117; and 5,021,428, which are divisions of U.S. Pat. No. 5,169, 096. See also U.S. Pat. No. 4,877,798 (fibromyalgia), U.S. Pat. No. 4,908,369 (insomnia); U.S. Pat. No. 5,106,855 (glaucoma); EP 319 962 (anxiety); EP 337 136 (extrapyramidal symptoms). All of the foregoing are incorporated herein by reference.

The COMPOUND was then specifically claimed in U.S. Pat. No. 5,134,149 which disclosed uses of antagonizing serotonin at the 5Ht2 receptor, treating anxiety, variant angina, anorexia nervosa, Raynaud's phenomenon, intermittent claudication, coronary or peripheral vasospasms, fibromyalgia, extrapyramidal symptoms, arrythmias, thrombotic illness, transient ischemic attacks, drug abuse, and psychotic illness such as schizophrenia and mania. See also U.S. Pat. Nos. 5,561,144; 5,700,812; 5,700,813; 5,721, 249—divisionals of U.S. Pat. No. 5,134,149—and also U.S. Pat. No. 5,618,824 (obsessive compulsive disorder) and PCT/US97/02597 (depressive disorders including major depressive episode and dysthymia, and bipolar disorder).

The COMPOUND is highly selective in its activity at the 5HT2a receptor compared to other receptors, and, as such, has reportedly fewer side effects. It has been shown to have a better CNS safety index relative to the reference compounds haloperiodol, clozapine, risperiodone, ritanserin, and amperozide in preclinical testing. JPET 277:968–981, 1996, incorporated herein by reference. It has recently been discovered that this COMPOUND is useful in the treatment of Sleep Disorders such as insomnia and obstructive sleep apnea.

Chronic insomnia among adults in the United States has been estimated to be present in ten percent of the adult population, and the annual cost for its treatment is estimated at $10.9 billion. JAMA 1997; 278: 2170–2177 at 2170. Chronic insomniacs report elevated levels of stress, anxiety, depression and medical illnesses. The most common class of medications for treating insomnia are the benzodiazepines, but the adverse effect profile of benzodiazepines include daytime sedation, diminished motor coordination, and cognitive impairments. Furthermore, the National Institutes of Health Consensus conference on Sleeping Pills and Insomnia in 1984 have developed guidelines discouraging the use of such sedative-hypnotics beyond 4–6 weeks because of concerns raised over drug misuse, dependency, withdrawal and rebound insomnia. JAMA 1997; 278: 2170–2177 at 2170. Therefore, it is desirable to have a pharmacological agent for the treatment of insomnia which is more effective and/or has fewer side effects that those currently used.

The prevalence of obstructive sleep apnea is estimated to be approximately 1–10% in the adult population, but may be higher in elderly individuals. DIAGNOSTIC AND STATISTICAL MANUAL OF MENTAL DISORDERS $4^{th}$ ed., American Psychiatric Association, Washington D.C. Preliminary evidence suggests that having obstructive sleep apnea may contribute to increased susceptibility to cardiovascular complications such as hypertension, cardiac arrhythmias, stroke, and myocardial infarction. Excessive daytime sleepiness is also a major complication.

Currently, the therapies used to treat obstructive sleep apnea include weight loss for the obese patient, Nasal-continuous positive Airway Pressure (a facemask used at night which produces a positive pressure within the upper airway), pharyngeal surgery and the administration of a variety of pharmacologic agents which have not been proven to be entirely successful. Chest 109 (5):1346–1358 (May 1996) entitled Treatment of Obstructive Sleep Apnea, a Review, hereby incorporated by reference. These agents include Acetazolamide, Medroxyprogesterone, Opioid Antagonists, Nicotine, Angiotensin-Convertying Enzyme Inhibitors and Psychotropic Agents (including those that prevent the reuptake of biogenic amines such as norepinephreine, dopamine and serotonin). Id. At 1353. Many of these pharmacological agents used also have a ventilatory depressant action (such as benzodiazepines) or other side effects such as urinary hesitancy and/or impotence in men (Protriptyline) so that a new agent with fewer side effects is needed for the treatment of obstructive sleep apnea. Even though serotonin is a sleep-inducing agent and may be a ventilatory stimulant (Id. At 1354), the COMPOUND of the present invention, which inhibits serotonin at the 5HT2a receptor, has been found useful in treating obstructive sleep apnea. See also Am. J. Respir Crit Care Med (153) pp 776–786 (1996) where serotonin antagonists exacerbated sleep apnea produced in English bulldogs. But compare, Journal of Physiology (466) pp 367–382 (1993), where it is postulated that an excess of serotonin due to dysfunction of the serotonin biosynthesis mechanisms might set up conditions which favor obstructive apneas; European Journal of Pharmacology (259):71–74 (1994) further work on rat model with 5ht2 antagonist.

Insomnia and Obstructive Sleep Apnea are sometimes found in conjunction with other conditions and sometimes those conditions are treatable by the COMPOUND, e.g., patients suffering from fibromyalgia may also have insomnia and/or sleep apnea. Am J Med Sci 1998; 315(6):367–376. Having one pharmacological agent which treats two or more existing or potential conditions, as does the present invention, is probably more cost effective, leads to better compliance and has fewer side effects than taking two or more agents.

It is an object of the present invention to provide a therapeutic agent for the use in treating Sleep Disorders. It is another object of the present invention to provide one pharmaceutical agent which may be useful in treating two or more conditions wherein one of the conditions is insomnia or sleep apnea and other Conditions respond to treatment by the COMPOUND.

Subjective and Objective Determinations of Sleep Disorders

There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times does the patient wake up during the night, how restless is the patient during sleep, etc. Another method is to objectively measure the stages of sleep.

Polysomnography is the monitoring of multiple electro-physiological parameters during sleep and generally includes measurement of EEG activity, electroculographic activity and electromyographic activity, as well as other measurements. These results, along with observations, can measure not only sleep latency (the amount of time required to fall asleep), but also sleep continuity (overall balance of sleep and wakefulness) which may be an indication of the quality of sleep.

There are five distinct sleep stages which can be measured by polysomnogrpahy: rapid eye movement (REM) sleep and four stages of no-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 50% of time spent asleep. Stages 3 and 4 NREM sleep (also known collectively as slow-wave sleep) are the deepest levels of sleep and occupy about 10–20% of sleep time. REM sleep, during which the majority of typical story like dreams occur, occupies about 20–25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night. Alternating with NREM sleep about every 80–100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

SUMMARY OF THE INVENTION

The present invention comprises a method of treating a patient for a Sleep Disorder by administering to the patient a therapeutically sufficient amount of R-(+)-α-(2,3-Dimethoxyphenyl)-1-[2-(4-fluorophenyl)ethyl]-4-piperidinemethanol or a pharmaceutically acceptable salt thereof. The Sleep Disorder can be Insomnia (Primary Insomnia, Insomnia related to another Mental Disorder, or Substance-Induced Insomnia) or Obstructive Sleep Apnea.

The present invention also comprises monotherapy for treating a Sleep Disorder and another Condition treatable by administration of R-(+)-α-(2,3-Dimethoxyphenyl)-1-[2-(4-fluorophenyl)ethyl]-4-piperidinemethanol or a pharmaceutically acceptable salt thereof. Examples of other Conditions treatable by administration of R-(+)-α-(2,3-Dimethoxyphenyl)-1-[2-(4-fluorophenyl)ethyl]-4-piperidinemethanol or a pharmaceutically acceptable salt thereof are schizophrenia, fibromyalgia, obsessive compulsive disorder, coronary vasospams, thrombotic illness, angina, anorexia nervosa, Raynaud's phenomenon, extrapyramidal symptoms, anxiety, arrythmias, depressive disorders, and bipolar depression.

DETAILED DESCRIPTION OF THE INVENTION

As used herein, the following terms have these specified meanings:

a) the term "patient refers to a warm-blooded animal, such as for example, rats, mice, dogs, cats, guinea pigs, and primates such as humans;

b) the term "treat" refers to either preventing, providing symptomatic relief, or curing the patient's disease, disorder or condition;

c) the term "administering" comprises administration via any appropriate route such as oral, sublingual, buccal, transdermal, inhalation, rectal or injection (including intramuscular, intravenous, subcutaneous, etc.), or any other appropriate method of providing the COMPOUND to the patient;

d) The term "therapeutically sufficient amount" means enough of the COMPOUND which becomes bioavailable through the appropriate route of administration to treat the patient for the disorder, condition or disease;

e) The term "pharmaceutically acceptable salt" means either an acid addition salt or a basic addition salt which is compatible with the treatment of patients for the intended use. "Pharmaceutically acceptable acid addition salt" is any non-toxic organic or inorganic acid addition salt of the base compounds represented by Formula I. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points. "Pharmaceutically acceptable basic addition salts" means non-toxic organic or inorganic basic addition salts of the compounds of Formula (I), if it can be made. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection of the appropriate salt may be important so that the ester is not hydrolyzed. The selection criteria for the appropriate salt will be known to one skilled in the art.

f) The term "Restorative Sleep" means sleep which produces a rested state upon waking;

g) the term "Sleep Disorder" means Insomnia and Obstructive Sleep Apnea;

h) the term "Insomnia" means Primary Insomnia, Insomnia related to another Mental Disorder, and Substance-Induced Insomnia;

i) The term "Primary Insomnia" means difficulty in initiating sleep, in maintaining sleep or having restorative sleep which is not caused by a Mental Disorder or due to physiological effects of taking or withdrawing from certain substances (substance-induced). As used herein, it also includes Circadian Rhythm Insomnia which is insomnia due to a change in the normal sleep-wake schedule (shift changes, jet lag, etc.);

j) The term "Insomnia related to another Mental Disorder" means difficulty in initiating sleep, in maintaining sleep or having restorative sleep which is caused by an underlying Mental Disorder such as, for example, depression, anxiety or schizophrenia;

k) The term "Substance-Induced Insomnia" means difficulty in initiating sleep, in maintaining sleep or having restorative sleep which is caused by physiological effects of taking or withdrawing from certain substances such as caffeine, alcohol, amphetamine, opioids, sedatives, hypnotics and anxiolytics; and l) The term "Obstructive Sleep Apnea" means repeated episodes of upper-airway obstruction during sleep and is normally characterized by loud snores or brief gasps that alternate with episodes of silence.

The COMPOUND may be synthesized by methods known in the art, such as one previously described in U.S. Pat. No. 5,134,149, incorporated herein by reference,

SCHEME I

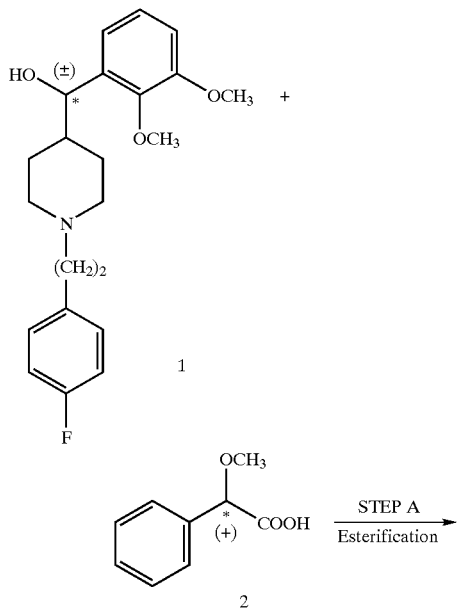

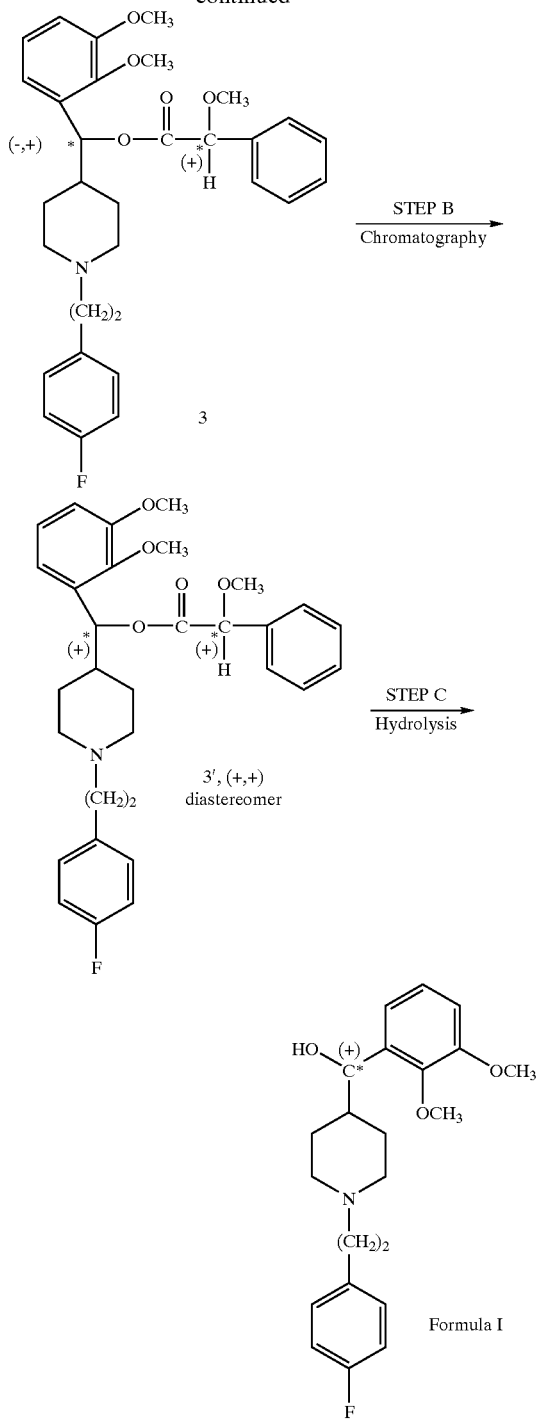

In Step A of Reaction Scheme I, an esterification reaction is carried out between racemic α-(2,3-dimethoxyphenyl)-1-[2-(4-fluorophenyl)ethyl]-4-piperidinemethanol (structure 1) and the (+)-isomer of α-methoxyphenylacetic acid (structure 2). This esterification produces the diastereomeric mixture identified as structure 3. These diastereomers are subjected to silica gel chromatography which separates the two diastereomers, thereby isolating the (+,+) diastereomer as is depicted in Step B. In Step C, the (+,+) diastereomer is hydrolyzed which produces the (+)-isomer of α-(2,3-dimethoxyphenyl)-1-[2-(4-fluorophenyl)ethyl]-4-piperidinemethanol.

The esterification reaction can be carried out using techniques known in the art. Typically approximately equivalent amounts of racemic α-(2,3-dimethoxyphenyl)-1-[2-(4-fluorophenyl)ethyl]-4-piperidinemethanol and the (+)-isomer of α-methoxyphenylacetic acid are contacted in an organic solvent such as methylene chloride, THF, chloroform, toluene and heated to reflux for a period of time ranging from 5 to 24 hours. The esterification is typically carried out in the presence of an equivalent amount of dicyclohexylcarbodiimide and a catalytic amount of 4-dimethylaminopyridine. The resulting diastereomers can be isolated by filtration of the dicyclohexylurea and evaporation of the filtrate.

The diastereomers are then subjected to silica gel chromatography which separates the (+,+) and the (−,+) diastereomers. This chromatographic separation may be carried out as is known in the art. A 1:1 mixture of hexane and ethyl acetate is one suitable eluent.

The resulting (+,+) diastereomer is then subjected to a hydrolysis reaction which produces the (+)-isomer of α-(2,3-dimethoxyphenyl)-1-[2-(4-fluorophenyl)ethyl]-4-piperidine-methanol. The hydrolysis is carried out by contacting the diastereomer with an excess of a base such as potassium carbonate in an aqueous alcoholic solution. The hydrolysis is carried out at a temperature of about 15 to 30° C. for a period of time ranging from 2 to 24 hours. The resulting (+)-isomer of α-(2,3-dimethoxyphenyl)-1-[2-(4-fluorophenyl)ethyl]-4-piperidinemethanol may then be recovered by dilution with water and extraction with methylene chloride. It is then purified by recrystallization from a solvent system such as cyclohexane/hexane or ethyl acetate/hexane.

Methods for producing the starting materials of Reaction Scheme I are known in the art. For example, U.S. Pat. No. 4,783,471 teaches how to prepare racemic α-(2,3-dimethoxyphenyl)-1-[2-(4-fluorophenyl)ethyl]-4-piperidine-methanol. This patent is hereby incorporated by reference. Examples No. 1 and 2 of this application also teach suitable methods. Alternatively, racemic α-(2,3-dimethoxyphenyl)-1-[2-(4-fluorophenyl)ethyl]-4-piperidinemethanol can be prepared in the following manner. Initially 4-hydroxypiperidine is subjected to an N-alkylation reaction with p-fluorophenylethyl bromide which produces 4-hydroxy-1-[2-(4-fluorophenyl)ethyl]-piperidine. This compound is brominated with $Ph_3P.Br_2$ which produces 4-bromo-1-[2-(4-fluorophenyl)ethyl]piperidine. This compound is contacted with Mg thereby forming a Grignard Reagent which is then reacted with 2,3-dimethoxybenzaldehyde which produces the desired product (±)-α-(2,3-dimethoxyphenyl)-1-[2-(4-fluorophenyl)ethyl]-4-piperidinemethanol. The (+)-isomer of α-methoxyphenylacetic acid is known in the art.

Examples 1, 2 and 3 show one method of making the COMPOUND. Examples 4 and 5 provide data on the method of using the COMPOUND.

EXAMPLE 1

Example 1, Steps A–D, demonstrates the preparation of the starting material (±)-α-(2,3-dimethoxyphenyl)-1-[2-(4-fluorophenyl)ethyl]-4-piperidinemethanol, structure 1.

A) 1-[2-(4-Fluorophenyl)ethyl]-4-piperidinecarboxamide

A solution of isonipectoamide (10.9 g, 85.0 mmol), 2-(4-fluorophenyl)ethyl Bromide (15.7g, 77.3 mmol), and $K_2CO_3$ (2.3 g, 167 mmol) was prepared in DMF (280 mL) and stirred under argon at 90–95° C. overnight. The cooled solution was concentrated to a white oily solid. The solid was partitioned between water and $CH_2Cl_2$. The layers were separated and the aqueous layer was extracted with $CH_2Cl_2$. The combined organic layers were washed 2× with water, dried ($MgSO_4$), filtered, and evaporated to an oily solid. The solid was recrystallized from EtOAc to afford 1-[2-(4-fluorophenyl)ethyl]-4-piperidinecarboxamide as a white powder, m.p. 177–178° C. (decomp.). Anal. Calcd. for $C_{14}H_{19}FN_2O$: C, 67.18; H, 7.65: N, 11.19. Found: C, 67.25; H, 7.67; N, 11.13.

B) 4-Cyano-1-[2-(4-fluorophenyl)ethyl]piperidine

To stirred phosphorus oxychloride (25 ml, 41.12 g, 268 mmol) and sodium chloride (5.1 g, 87.3 mmol) was added 1-[2-(4-fluorophenyl)ethyl]-4-piperidinecarboxamide (8.9 g, 35.6 mmol) portionwise. After complete addition, the solution was refluxed for 2 hours. The cooled solution was poured into dilute $NH_4OH$ to destroy the $POCl_3$. The aqueous solution was cooled to 0° C., then extracted 2× with $CH_2Cl_2$. The combined organic layers were dried ($MgSO_4$), filtered, and evaporated to afford 8.1 g of an oily solid. The solid was distilled, (b.p. 150° C., 0.1 mm Hg), to afford a clear, colorless oil that solidified. This material was crystallized from hexane to afford 4-cyano-1-[2-(4-fluorophenyl)ethyl]piperidine as white needles, m.p. 47–48° C. Anal. Calcd. for $C_{14}H_{17}FN_2$: C, 72.39; H, 7.38; N, 12.06. Found: C, 72.62; H, 7.49; N, 12.12.

C) 1-[2-(4-Fluorophenyl)ethyl]-4-piperidinecarboxaldehyde

To a stirred solution of 4-cyano-1-[2-(4-fluorophenyl)ethyl]piperidine (1.00 g, 4.3 mmol) in THF (20 mL) under argon at 0° C. was added DIBAL-H (4.6 mL of a 1.0 M solution in THF, 4.6 mmol) via syringe. After stirring overnight at room temperature, 10% aqueous HCl (25 mL) was added and the solution was stirred for 3 hours. The entire mixture was then poured into 10% aqueous NaOH (50 mL), then extracted 2× with ether. The combined organic layers were washed with brine, dried ($MgSO_4$), filtered, and evaporated to afford a pale yellow oil. The oil was chromatographed on silica gel, eluting with EtOAc. The appropriate fractions were combined and evaporated to afford an oil. This oil was distilled (b.p. 166° C., 0.05 mm Hg) to afford 1-[2-(4-fluorophenyl)ethyl]-4piperidinecarboxaldehyde, obtained as a colorless oil. Anal. Calcd. for $C_{14}H_{18}FNO$: C, 71.46; H, 7.71; N, 5.95. Found: C, 71.08; H, 7.81; N, 5.86.

D) (±)-α-(2,3-Dimethoxyphenyl)-1-[2-(4-fluorophenyl) ethyl]-4-piperidinemethanol To a stirred solution of veratrole (0.93 g, 6.7 mmol) in THF (20 mL) under argon at 0° C. was added n-BuLi (2.7 mL of a 2.5 M solution in hexane, 6.75 mmol). After stirring 2.5 h, the solution was cooled to −78° C. and treated with 1-[2-(4-fluorophenyl)ethyl]-4-piperidinecarboxaldehyde (1.30 g, 5.5 mmol) in THF (25 mL) via an additional funnel. The cooling bath was removed and the solution was allowed to stir for 2 hours. Water was added, the layers separated, and the aqueous layer was extracted with EtOAc. The combined organic layers were washed with brine, dried ($MgSO_4$), filtered, and chromatographed on silica gel, eluting with acetone. The appropriate fractions were combined and evaporated to afford a white solid. The solid was recrystallized from hexane to afford racemic α-(2,3-dimethoxyphenyl)-1-[2-(4-fluorophenyl)ethyl]-4- piperidinemethanol as shiny white needles, m.p. 126–127° C. Anal. Calcd. for $C_{22}H_{28}FNO_3$: C, 70.75; H, 7.56; N, 3.75. Found: C, 70.87; H, 7.65; N, 3.68.

EXAMPLE 2

Example 2, Steps A–F, demonstrate an alternative manner of preparing (±)-α-(2,3-dimethoxyphenyl)-1-[2-(4-fluorophenyl)ethyl]-4-piperidinemethanol, structure 1.

A) 1-(1,1-Dimethylethyl)-1,4-piperidinedicarboxylic Acid

To isonipecotic acid (107.5 g, 832 mmol) stirred in 1N NaOH (40 g NaOH in 900 mL $H_2O$) and tert-butanol (1800 mL) was added di-tert-butyl dicarbonate (200 g, 916 mmol) in portions. After stirring overnight, the solution was concentrated and the resulting water layer was extracted 3× with ether. The combined organic layers were washed with water, brine, dried ($MgSO_4$), filtered, and evaporated to a white solid, which was recrystallized from EtOAc/hexane (300 mL/200 mL) to afford 1-(1,1-dimethylethyl)-1,4-piperidinedicarboxylic acid as white needles, m.p. 147–149° C.

B) 4-(N-methoxy-N-methylcarboxamido)-1-piperidinecarboxylic acid 1,1-dimethylethyl Ester To a stirred solution of 1-(1,1-dimethylethy)-1,4-piperidinedicarboxylic acid (50.0 g, 218 mmol) in anhydrous $CH_2Cl_2$ (500 mL) under $N_2$ in a 2L flask was added 1,1'-carbonyldiimidazole (38.9 g, 240 mmol) portionwise. After stirring for 1 hour, N,O-dimethylhydroxylamine hydrochloride (23.4 g, 240 mmol) was added in one portion. After stirring overnight, the solution was washed twice with 1N HCl, twice with saturated $NaHCO_3$, once with brine, dried ($MgSO_4$), filtered, and evaporated to an oil. Distillation afforded 4-(N-methoxy-N-methylcarboxamido)-1-piperidinecarboxylic acid 1,1-dimethylethyl ester as a clear oil, b.p. 120–140° C., 0.8 mm.

C) 4-(2,3-Dimethoxybenzoyl)-1-piperidinecarboxylic Acid 1,1-dimethylethyl Ester n-Butyl lithium (14.5 mL of a 2.5 M solution in hexane, 36.3 mmol) was added via syringe to a stirred solution of veratrole (5.00 g, 36.2 mmol) in THF (50 mL, anhydrous) under argon at 0° C. The ice bath was removed and the mixture was allowed to stir for 90 minutes. The mixture was cooled to −78° C. and treated with 4-(N-methoxy-N-methylcarboxamido)-1-piperidinecarboxylic acid 1,1-dimethylethyl ester (9.20 g, 33.8 mmol) in THF (50 mL, anhydrous) via syringe. The cooling dry ice-acetone bath was removed and the mixture was allowed to come to room temperature. After stirring for 3 hours, saturated aqueous $NH_4Cl$ was added and the mixture was allowed to stir overnight. The layers were separated and the aqueous layer was extracted with ether. The combined organic layers were washed with brine, dried ($MgSO_4$), filtered, and evaporated to afford an amber oil. The oil was chromatographed on silica gel, eluting with 20% EtOAc in hexane. The appropriate fractions were combined and evaporated to an amber oil. The oil was distilled to afford 4-(2,3-dimethoxybenzoyl)-1-piperidinecarboxylic acid 1,1-dimethylethyl ester as a colorless oil. (b.p. 225–250° C., 0.05 mm). Anal. Calcd. for $C_{19}H_{27}NO_5$: C, 65.31; H, 7.79; N, 4.01. Found: C, 65.04; H, 7.92; N, 4.11.

D) 4-(2,3-Dimethoxyphenyl)-4-piperidinylmethanone 4-(2,3-Dimethoxybenzoyl)-1-piperidinecarboxylic acid 1,1-dimethylethyl ester (7.75 g, 22.2 mmol) was dissolved in trifluoroacetic acid (50 mL, 650 mmol) and stirred for 45 minutes. The entire solution was poured into ether (900 mL) and allowed to stand overnight. Filtration yielded 4-(2,3-dimethoxyphenyl)-4-piperidinylmethanone trifluoroacetate as fine white needles, m.p. 123° C. Anal. Calcd. for $C_{14}H_{19}NO_3 \cdot CF_3CO_2H$: C, 52.89; H, 5.55; N, 3.86. Found: C, 52.77; H, 5.62; N, 3.82.

The resulting 4-(2,3-dimethoxyphenyl)-4-piperidinylmethanone trifluoroacetate was dissolved in water, treated with NaOH (10% aqueous) until basic, and extracted three times with dichloromethane. The combined organic layers were washed with brine, dried ($MgSO_4$), filtered and evaporated to afford 4-(2,3-dimethoxyphenyl)-4-piperidinylmethanone as an oil.

E) (2,3-Dimethoxyphenyl)[1-[2-(4-fluorophenyl)ethyl]-4-piperidinyl]methanone monohydrochloride A solution of 4-(2,3-dimethoxyphenyl)-4-piperidinylmethanone (8.00 g, 32.1 mmol) and 2-(4fluorophenyl)ethyl bromide (6.52 g, 32.1 mmol) was prepared in DMF (90 mL) treated with $K_2CO_3$ (7.0 g, 50.7 mmol), then stirred and heated at 80° C. under argon overnight. The cooled solution was poured into a partition of 2/1 EtOAc/toluene and water. The layers were separated and the aqueous layer was extracted with 2/1 EtOAc/toluene. The combined organic layers were washed 2× with water, 1× with brine, dried ($MgSO_4$), filtered, and evaporated to afford 11.0 g of an oil. The oil was chromatographed on silica gel, eluting with EtOAc. The appropriate fractions were combined, concentrated, dissolved in ethyl acetate and treated with HCl/ethyl acetate. (2,3-dimethoxyphenyl)[1-[2-(4-fluorophenyl)ethyl]-4-piperidinyl]-methanone monohydrochloride was obtained as a precipitate, m.p. 225–227° C. (decomp). Anal. Calcd. for $C_{22}H_{26}FNO_3 \cdot HCl$: C, 64.78; H, 6.67; N, 3.43. Found: C, 64.44; H, 6.73; N, 3.41.

F) (±)-α-(2,3-Dimethoxyphenyl)-1-[2-(4-fluorophenyl)ethyl]-4-piperidinemethanol To a stirred solution of (2,3-dimethoxyphenyl)[1-[2-(4-fluorophenyl)ethyl]-4-piperidinyl]-methanone (6.0 g, 16.2 mmol) in MeOH (100 mL) at 0° C. was added $NaBH_4$ (1240 mg, 32.8 mmol) in two portions, over an one hour period. After stirring overnight, the solution was concentrated to a solid. The solid was partitioned between water and ether. The layers were separated and the aqueous layer was extracted with ether. The combined organic layers were washed with brine, dried ($MgSO_4$), filtered, and evaporated to a solid. The solid was chromatographed on silica gel, eluting with acetone. The appropriate fractions were combined and evaporated to afford a white solid. The solid was recrystallized from cyclohexane to afford (±)-α-(2,3-dimethoxyphenyl)-1-[2-(4-fluorophenyl)-ethyl]-4-piperidinemethanol as white needles, m.p. 126–127° C. Anal. Calcd. for $C_{22}H_{28}FNO_3$: C, 70.75; H, 7.56; N, 3.75. Found: C, 70.86; H, 7.72; N, 3.93.

EXAMPLE 3

This example demonstrates the preparation of the compound of Formula-I.

Preparation of (+)-α-(2,3-Dimethoxyphenyl)-1-[2-(4-fluorophenyl)ethyl]-4-piperidinemethanol

A) Preparation of Diastereomers

A solution of 3.90 g (10.4 mmol) of (±)-α-(2,3-dimethoxyphenyl)-1-[2-(4-fluorophenyl)ethyl]-4- piperidinemethanol, 1.74 g (10.4 mmol) of S-(+)-α-methoxyphenylacetic acid, 2.15 g (10.4 mmol) of 1,3-dicyclohexylcarbodiimide and 0.1 g of 4-dimethylaminopyridine in chloroform (75 mL) was refluxed for 17 hours, allowing to cool to room temperature and filtered. The filtrate was concentrated and chromatographed on a silica gel column eluting with ethyl acetate/hexane (1:1) to afford two diastereomers, Rf=0.1 and 0.2 (TLC EtOAc/hexane, 1:1). Intermediate fractions were re-chromatographed to give additional material. Those fractions with Rf=0.2 were combined to give a single diastereomeric ester, (+,+)-(2,3-dimethoxyphenyl)[1-[2-(4-fluorophenyl)ethyl]-4-piperidinyl]methyl-α-methoxybenzene-acetate.

B) Preparation of (+)-α-(2,3-dimethoxyphenyl)-1-[2-(4-fluorophenyl)ethyl]-4-piperidinemethanol To a stirred solution of 0.97 g (1.9 mmol) of the above mentioned diastereomeric ester, Rf=0.2, in 25 mL of methanol was added 0.5 g (3.6 mmol) of potassium carbonate and 5.0 mL of water. After stirring 17 hours at room temperature the reaction mixture was diluted with water and extracted twice with methylene chloride. The combined extracts were washed with water, brine and dried over $MgSO_4$. After filtering, the filtrate was concentrated to an oil and crystallized from 40 mL of cyclohexane/hexane (1:1) to give (+)-α-(2,3-dimethoxyphenyl)-1-[2-(4-fluorophenyl)ethyl]-4-piperidinemethanol, m.p. 112–113° C., $[\alpha]_D^{20}=+13.9°$.

The COMPOUND can be formulated into pharmaceutical dosage forms using techniques well known in the art. For oral administration, the compound can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compound can be tableted with conventional tablet bases such as lactose, sucrose, and cornstarch in combination with binders, such as acacia, cornstarch, or gelatin, disintegrating agents, such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compound or its salts may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetable, or synthetic origin. The pharmaceutical carrier may also contain preservatives, buffers, etc. as are known in the art.

The dosage range at which the COMPOUND exhibits its ability to treat Sleep Disorders, including each specific type of Sleep Disorder, can vary depending upon the specific disorder, its severity, the patient, any underlying disease states that the patient is suffering from, and other medications that may be concurrently administered to the patient. Generally though, this COMPOUND will exhibit its ability to treat Sleep Disorders at a range of 0.001 mg/kg/day to about 100 mg/kg/day. It may be delivered by any appropriate means, such as orally, sublingually, buccally, transdermally, rectal via suppository, inhalation or injection.

EXAMPLE 4

A) In five healthy subjects received a single 10 mg dose of the COMPOUND and seven subjects received a single 20 mg dose of the COMPOUND administered orally. Forty percent of the subjects receiving the 20 mg dose (2 out of 5) and sixty percent of the subjects receiving the 10 mg dose (3 out of 5) experienced mild to moderate sedation.

B) Forty-nine patients diagnosed with schizophrenia received either 10 mg of the COMPOUND (5 mg twice daily), 20 mg of the COMPOUND (10 mg twice daily), 40 mg of the COMPOUND (20 mg twice daily) or placebo orally twice daily. The following was reported:

|  | Placebo | 10 mg | 20 mg | 40 mg | Total |
|---|---|---|---|---|---|
| Insomnia | N = 1; 14.3% | N = 0; 0% | N = 3: 21.4% | N = 3; 23.1% | N = 7; 14.3% |
| Somnolence | N = 0; 0% | N = 3; 20% | N = 1; 15.4% | N = 2; 15.4% | N = 6; 12.2% |

The milligram (mg) amounts refer to the amount of the COMPOUND orally administered to the subjects and "n" refers to the number of subjects that reported the effect. This chart shows that although some insomnia was reported by some subjects having schizophrenia, some subjects also reported somnolence.

C) Doses of 36 mg, 72 mg, 108 mg and 138 mg of the COMPOUND and placebo were orally administered to healthy subjects. The following data were reported.

|  | Placebo | 9 mg | 18 mg | 36 mg | 72 mg | 108 mg | 138 mg |
|---|---|---|---|---|---|---|---|
| Drowsiness | n = 6 33% n = 3 | n = 4 50% n = 2 | n = 4 100% n = 4 | n = 4 100% n = 4 | n = 4 75% n = 3 | n = 4 100% n = 4 | n = 4 100% n = 4 |

The drowsiness was rated as mild or moderate at doses below 72 mg and moderate to severe at 72 mg and above.

D) In healthy subjects, the COMPOUND was administered in 3 mg (n=4), 9 mg (n=4), 18 mg (n=4), 36 mg (n=4) and 72 mg (n=4) doses along with the placebo (n=5) wherein "n" is the number of subjects. Only the group receiving the 72 mg dose reported drowsiness (n=3).

EXAMPLE 5

Intraperitoneal application of L-Tryptophan (10 mg/kg) and Pargyline (50 mg/kg) to anaesthetized newborn rats depressed the amplitude of the inspiratory discharges of the genioglossal muscle and induced obstructive apneas (OA). The following shows that the COMPOUND is efficient in preventing these effects and compares its efficiency to theophylline.

Experiments were carried out on newborn Sprague Dawley rats from Iffa Credo breeding center. The animals were anaesthetized by intraperitoneal injection of low doses of sodium pentobarbitone (7–10 mg/kg), kept lying (dorsal cubitus) on a warming blanket and were spontaneously ventilating.

The EMG activity of the genioglossal muscles and the diaphragm were recorded with fine insulated wires (bipolar recordings) inserted within the muscles, filtered (100–3,000 Hz), amplified (×5–10,000) and integrated (time constant 50 ms). The rib cage movements were recorded via a captor gently touching the lower ribs and/or the abdominal wall.

The air flow changes resulting from the respiratory chest movements were recorded via a facial mask and a highly sensitive pressure recorder.

Effects of Compound on Depression of Genioglossal EMG Induced by L-Tryptophan and Pargyline Ten to fifteen minutes after induction of anesthesia, the animals received first an intraperitoneal injection of the COMPOUND, and a control recording was taken to define the mean amplitude of the integrated EMGs. Then, the animal received an intraperitoneal injection of L-Tryptophan plus Pargyline ("L-Trp+Parg") 10 mg/kg and 50 mg/kg, respectively, and the changes in EMG amplitudes were checked every 10 minutes and were expressed as % of control values.

In ten animals, the pre-treatment with MDL 100,907 at 0.1 mg/kg did not prevent the depression of genioglossal (GG) discharge induced by injection of L-Trp+Parg. L-Trp+Parg injection significantly depressed by 30–50% the mean GG discharge for about 30 minutes. A larger dose of the COMPOUND (1 mg/kg) was applied in ten other newborn rats and this pre-treatment was now efficient in preventing the GG depression. Finally, ten more animals received the largest dose used of the COMPOUND (3 mg/kg) and confirmed the efficiency of the COMPOUND.

Effects of the Compound Pretreatment on the Occurrence of Obstructive Apnea Induced by L-Tryptophan and Pargyline Injection The respiratory movements and resulting air flow changes were measured in 30 newborn rats which received first a pre-treatment with the COMPOUND at either 0.1, 1 or 3 mg/kg and 10 min later L-Trp+Parg injection. L-Trp+Parg injection induced OAs in 9 of 10 newborn rats which received the COMPOUND at 0.1 mg/kg, and 4 of the 10 animals eventually died of respiratory distress, similar to animals from previous studies which received L-Trp+Prg alone.

Five out of ten newborn rats which received the COMPOUND at 1 mg/kg did not present short lasting OAs at all after L-Trp+Parg injection. Among the 5 of 10 newborn rats which displayed OAs, 2 animals had infrequent OAs (less than 5 short lasting OAs in 60 minutes). The mean curve calculated for the 1 mg/kg sample revealed a peak frequency of occurrence of short lasting OAs between 20–40 min after the injection (range 4 OAs per 10 minute period) which was significantly less than that observed in the 0.1 mg/kg sample. After 1 mg/kg pre-treatment with the COMPOUND, long lasting OAs were observed in only one newborn rat and all animals survived to L-Trp+Parg injection. Applying the largest dose of the COMPOUND (3 mg/kg) confirmed the COMPOUND efficiency in preventing OAs. Only 2 of 10 treated rats presented frequent short lasting Oas, 3 of 10 had a total of less than 3 short lasting Oas, and 5 of 10 showed no short lasting Oas. None of the 10 animals displayed long lasting OAs and all survived.

Effects of Theophylline Pre-Treatment on the Occurrence of Obstructive Apneas Induced by L-Tryptophan and Pargyline Injection Five newborn rats received theophylline at 10 mg/kg and 5 other animals received theophylline at 30 mg/kg. In both cases, L-Trp+Prg injection depressed the amplitude of GG inspiratory discharges and this effect was not prevented by either dose of theophylline. In a second set of experiments, induction of OAs after L-Trp+Prg injection also was not prevented by theophylline at 10 or 30 mg/kg.

What is claimed is:

1. A method of providing symptomatic relief from substance induced insomnia in a patient comprising administering to said patient a therapeutically effective amount of R-(+)-α-(2,3-dimethoxphenyl)-1-[2-(4-fluoropheyl)ethyl]-4-piperidinemethanol or a pharmaceutically acceptable salt thereof wherein said substance is selected from the group consisting of caffeine, alcohol, amphetamine, opioids, sedatives, hypnotics and anxiolytics.

2. The method of claim 1 wherein the substance is caffeine.

3. The method of claim 1 wherein wherein the substance is alcohol.

4. The method of claim 1 wherein the substance is amphetamine.

5. The method of claim 1 wherein the substance is an opiod.

6. The method of claim 1 wherein the substance is a sedative.

7. The method of claim 1 wherein the substance is a hypnotic.

8. The method of claim 1 wherein the substance is an anxiolytic.

9. A method of providing symptomatic relief from alcohol induced insomnia in a patient comprising administering to said patient a therapeutically effective amount of R-(+)-α-(2,3-dimethoxyphenyl)-1-[2-(4-fluorophenyl)ethyl]-4-piperidinemethanol or a pharmaceutically acceptable salt thereof.

10. The method of claim 9 wherein alcohol induced insomnia is caused by effects of taking alcohol.

11. The method of claim 9 wherein alcohol induced insomnia is caused by effects of withdrawing from alcohol.

12. A method of providing symptomatic relief from caffeine induced insomnia in a patient comprising administering to said patient a therapeutically effective amount of R-(+)-α-(2,3-dimethoxyphenyl)-1-[2-(4-fluorophenyl)ethyl]-4-piperidinemethanol or a pharmaceutically acceptable salt thereof.

13. The method of claim 12 wherein alcohol induced insomnia is caused by effects of taking caffeine.

14. The method of claim 12 wherein alcohol induced insomnia is caused by effects of withdrawing from caffeine.

* * * * *

UNITED STATES PATENT AND TRADEMARK OFFICE
CERTIFICATE OF CORRECTION

PATENT NO. : 6,939,879 B2
DATED : September 6, 2005
INVENTOR(S) : Cesare Mondadori et al.

It is certified that error appears in the above-identified patent and that said Letters Patent is hereby corrected as shown below:

<u>Title page,</u>
Item [60], Related U.S. Application Data, "Continuation of application No. 09/886,424, filed on Jun. 21, 2001, now Pat. No. 6,613,779, which is a continuation of application No. 09/382,932, filed on Aug. 23, 1999, now Pat. No. 6,277,864" should read -- Continuation of application No. 09/886,424, filed on Jun. 21, 2001, now Pat. No. 6,613,779, which is a continuation of application No. 09/382,932, filed on Aug. 25, 1999, now Pat. No. 6,277,864 --.

Signed and Sealed this

Fourth Day of April, 2006

JON W. DUDAS
*Director of the United States Patent and Trademark Office*